(12) United States Patent
Taylor et al.

(10) Patent No.: US 10,004,582 B2
(45) Date of Patent: *Jun. 26, 2018

(54) CUFF OF AN ARTIFICIAL URINARY SPHINCTER SYSTEM

(71) Applicant: Coloplast A/S, Humlebaek (DK)

(72) Inventors: Jeffrey Brian Taylor, Forest Lake, MN (US); Carly Aho, Long Prarie, MN (US); Michael B. Hektner, Minneapolis, MN (US); Steve Knop, Maple Grove, MN (US); Jessica Santos, Lino Lakes, MN (US)

(73) Assignee: Coloplast A/S, Humlebaek (DK)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/285,502

(22) Filed: Oct. 5, 2016

(65) Prior Publication Data
US 2017/0020644 A1    Jan. 26, 2017

Related U.S. Application Data

(63) Continuation of application No. 13/923,372, filed on Jun. 21, 2013, now Pat. No. 9,486,301.

(51) Int. Cl.
*A61F 2/04* (2013.01)
*A61F 2/00* (2006.01)

(52) U.S. Cl.
CPC ...... *A61F 2/004* (2013.01); *A61F 2230/0013* (2013.01)

(58) Field of Classification Search
CPC . A61F 2/004; A61F 2/0027; A61F 2230/0013
See application file for complete search history.

(56) References Cited

U.S. PATENT DOCUMENTS

2009/0018385 A1*  1/2009  Trubiano ............... A61F 2/0036
                                                                600/30
2014/0039242 A1*  2/2014  Domel .................. A61F 2/0036
                                                                600/30

* cited by examiner

*Primary Examiner* — Thaddeus Cox
(74) *Attorney, Agent, or Firm* — Coloplast Corp., Coloplast A/S; Nick Baumann (57) ABSTRACT

A cuff of an artificial urinary sphincter system includes a frame and an inflatable balloon. The frame has a first end spaced away from a second end by a gap, where the gap extends from a top edge to a bottom edge of the frame to provide an opening in the frame. The frame has a frame length measured along an interior surface of the frame from the first end to the send end of the frame to define a first quadrant that extends from the first end for a distance of about 25% of the frame length and a second quadrant that extends from the second end for a distance of about 25% of the frame length. A first inflatable balloon attached to the interior surface of the frame in the first quadrant of the frame.

9 Claims, 11 Drawing Sheets

CUFF OF AN ARTIFICIAL URINARY SPHINCTER SYSTEM

BACKGROUND

Urinary incontinence affects about 200 million people worldwide and about 25 million people in the US. Urinary incontinence is generally more prevalent in women than in men.

Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a portion of the urethra. The artificial sphincter has a closed position that selectively prevents the flow of urine through the urethra, thus providing the user with a comfortable, continent state. The artificial sphincter can be activated to an open position by the user, which opens the urethra and allows the user to selectively pass urine.

Surgeons and patients would welcome advances in the treatment of urinary incontinence.

SUMMARY

One aspect provides an artificial urinary sphincter (AUS) system having a pump attachable with tubing between a pressure regulating reservoir and a cuff. The cuff is configured for placement around a portion of a urethra and has a frame with at least one inflatable balloon attached to the frame. A gap is formed from a top edge to a bottom edge of the frame, where the gap provides the rigid frame with a C-shaped conformation in lateral cross-section having a first lateral section separated from a second lateral section. Each inflatable balloon(s) is/are attached to an interior surface on one of the first lateral section or the second lateral section of the frame.

One aspect provides an artificial urinary sphincter system including a pump attachable with tubing between a pressure regulating reservoir and a cuff. The cuff is configured for placement around a portion of a urethra and has a rigid frame with at least one inflatable balloon attached to the rigid frame. A gap is formed from a top edge to a bottom edge of the rigid frame, where the gap provides the rigid frame with a C-shaped conformation in lateral cross-section having a first lateral section separated from a second lateral section. Each inflatable balloon(s) is/are attached to an interior surface on one of the first lateral section or the second lateral section of the rigid frame.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

As employed in this specification, "end" means endmost or the very end point of the subject being described, and "end portion" means that segment that is immediately adjacent to the end of the subject being described.

As employed in this specification, "rigid" means that the referenced material or component does not deform noticeably for pressures applied to the material or component between 1-120 cm H2O. For example, the disclosure describes a cuff having a rigid frame, and the rigid frame supports an inflatable balloon on its interior surface. Inflating the balloon causes the balloon to expand against the interior surface of the cuff, which will have a tendency to expand the frame of the cuff outward and potentially diminish pressure applied from the balloon to the urethra. The frame of the cuff is configured to not expand, and thus its lateral dimensions are said to remain substantially unchanged, for a pressure applied to the interior surface of the rigid frame by the inflatable balloons of less than 120 cm H2O. In this manner, the rigid frame allows the cuff to efficiently deliver the energy from expansion of the balloon to the urethra.

One urinary control system that has found favor with the medical community includes three components cooperatively attached with kink-resistant tubing: an occlusive cuff, a control pump, and a pressure-regulating balloon reservoir. The cuff is implanted around the urethra. The control pump is implanted in the scrotum of a male user. The pressure-regulating balloon reservoir is implanted in the prevesical space, for example through a suprapubic incision followed by dissection of the rectus fascia and a spreading of the linea alba. The three components are filled with liquid (saline) to provide a liquid-filled closed system maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra. The cuff is fabricated from sheets of film that are sealed to provide one or more inflatable cushions. The cuff is provided in a rectangular shape and is intended to be placed around the urethra. Typically, the surgeon dissects tissue away from the urethra, including the tissue posterior to the urethra that is blocked from the surgeon's view. Thus, the surgeon employs a blind approach to place the cuff in a circular fashion around the urethra. The ends of the rectangular cuff are secured together, which ensures that the cuff remains around the urethra. Observers have noticed that the cuff of this three component system has a tendency to kink when it inflates, particularly at the junction of where the rectangular balloon cushions are formed into a circular cuff. The location of the kink can wear over time and create a leak in the cuff.

Embodiments described in this application provide an artificial urinary sphincter (AUS) system having a cuff that configured for placement around most of the urethra without dissecting tissue posterior to the urethra. Embodiments described below provide a cuff having a frame formed in a C-shape that allows the surgeon to guide the open portion of the C-shape over the urethra. The C-shaped cuff obviates the need to dissect the tissue posterior to the urethra. The C-shaped cuff offers a more efficient implantation approach since the backside of the urethra is not visible to the surgeon as s/he dissects tissue, which poses a possible risk of nicking the urethra when dissecting tissue. The cuff described below reduces the amount of dissection behind the urethra in the blind area that the surgeon needs to complete prior to placement of the cuff.

The expansion balloons of the cuff expand into an interior space of the frame and have reduced or eliminated kinking.

The AUS system described in this patent application is suited for use both in female patients and in male patients, where the cuff is placed around a portion of the urethra. Female patients will have the pump component implanted in one of the labia or in an abdominal area. Male patients will have the pump component implanted in the scrotum.

Figure 1:
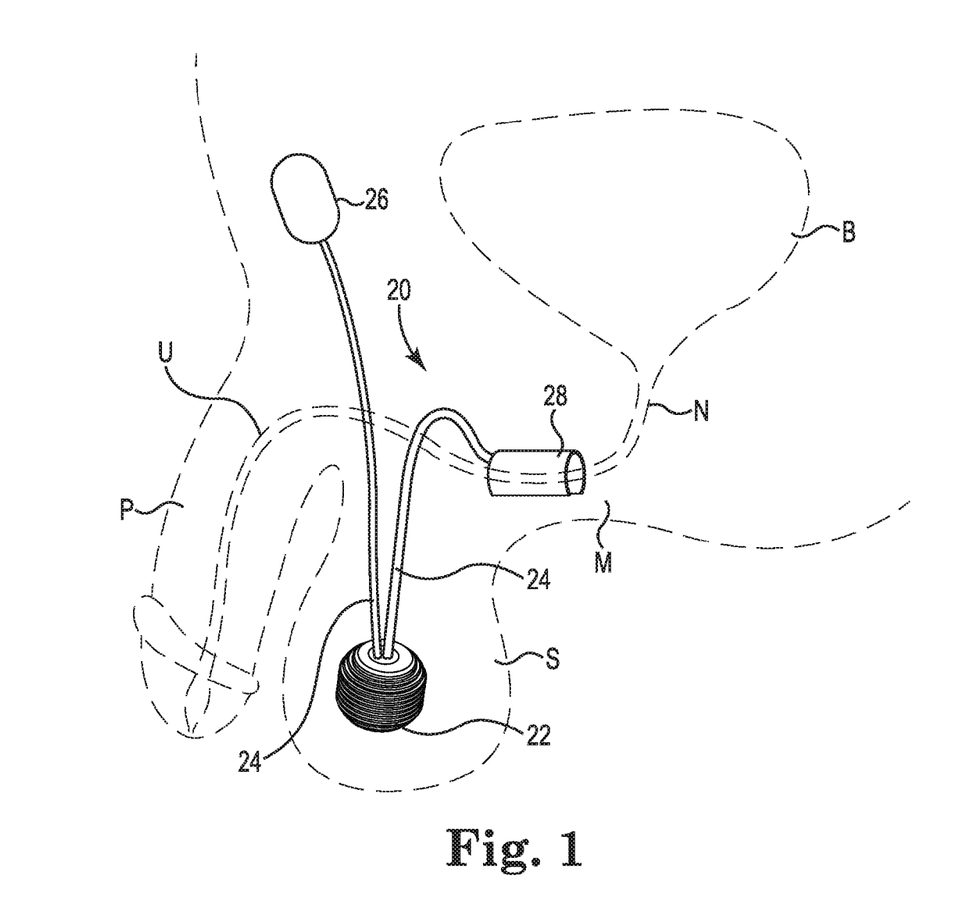
FIG. 1 is a perspective view of one embodiment of an artificial urinary sphincter (AUS) system implanted in a male patient.

FIG. 1 is a perspective view of one embodiment of an artificial urinary sphincter (AUS) system 20 illustrated as implanted in the environment of the male urogenital region. The AUS system 20 includes a pump 22 attachable with tubing 24 between a pressure regulating reservoir 26 and a cuff 28.

The pump 22 is typically implanted within the scrotum S, which provides access to the pump 22 by the user. Other locations for placement of the pump 22 are also acceptable, for example as determined by the gender of the user.

The pump 22 is operable to inflate one or more balloons associated with the cuff 28. One suitable pump 22 is the suction style pump bulb as illustrated that cooperates with the cuff 28. Other suitable pump mechanisms are also acceptable, including electromechanical pumps, electronic pumps, button-style cavity pumps, and the like.

The tubing 24 is provided in a kink resistant form and includes some style of connector that allows segments of the tubing 24 to be attached together after the various components (the reservoir 26 and the cuff 28) are primed with liquid. The tubing 24 is generally a thin-walled tube that is attachable between the pump 22 and the reservoir 26, and between the pump 22 and the cuff 28. In one embodiment, the tubing 24 is separate from the pump 22 and separate from the reservoir 26/cuff 28 and connects to these components through a locking mechanism, such as a quick connector or other suitable snap-fit connector.

The reservoir 26 is sized to retain a volume of liquid at an equilibrium pressure that is selected to ensure that the inflatable balloons of the cuff 28 operate to coapt the urethra. The reservoir 26 maintains the pressure in the closed system 20 after the tubing 24 is connected between the components.

The cuff 28 is implanted around the bulbous urethra or around the portion of the urethra descending from the bladder neck N. The cuff 28 is sized to allow placement as close to the bladder B as possible (desired by some surgeons), or positioned distal the bladder neck N as suitably determined by the attending surgeon. As illustrated in FIG. 1, the cuff 28 is implanted around the urethra U at a location where the urethra U transitions from a vertical orientation communicating with the bladder B to a horizontal orientation extending to the penis P, which desirably corresponds to the area of the urogenital region associated with an increased level of muscle M mass.

Figure 2:
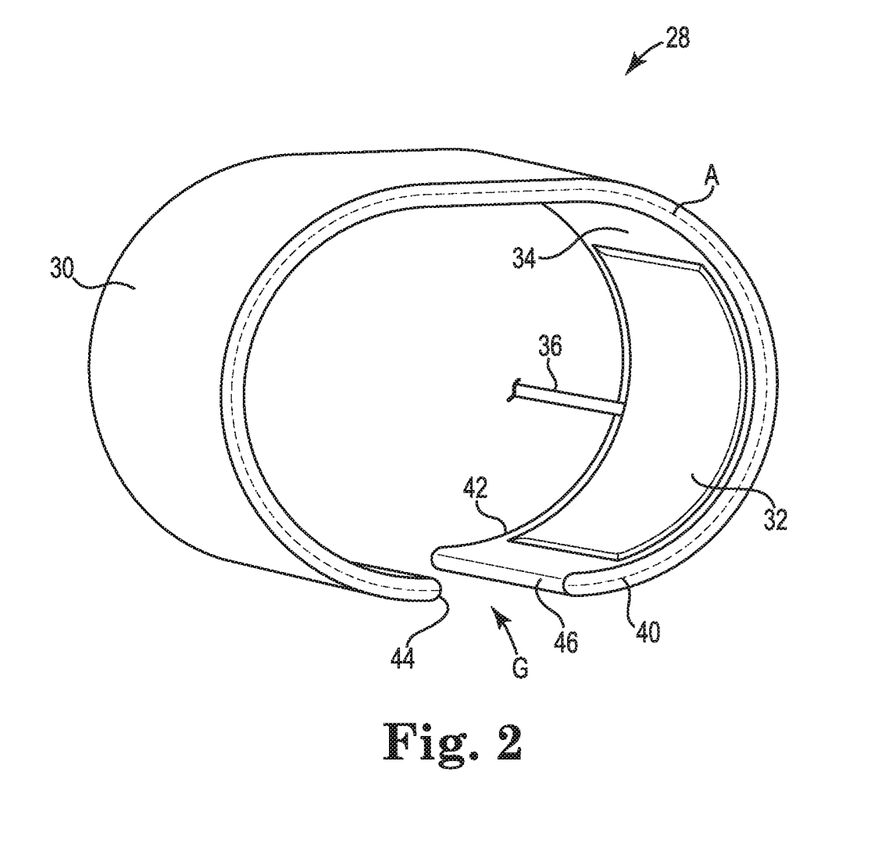
FIG. 2 is a perspective view of one embodiment of a cuff of the system illustrated in FIG. 1 including an inflatable balloon in a deflated state.

FIG. 2 is a perspective view of one embodiment of the cuff 28. The cuff 28 includes a rigid frame 30 and an inflatable balloon 32 attached to an interior surface 34 of the rigid frame 30. The inflatable balloon 32 is illustrated in a deflated configuration. The inflatable balloon 32 is provided with a connector 36 that is suitable for attachment to the tubing 24 (FIG. 1).

The frame 30 maintains the shape and integrity of the cuff 28. The frame supports an axial pushing force, which allows the cuff 28 to be pushed past tissue and directed around and behind a blindside portion of the urethra during implantation. The cuff 28 includes a gap G that is formed from a top edge 40 to a bottom edge 42 of the rigid frame 30, such that the gap G extends between a first end 44 and a second end 46 of the frame 30. The G is sized to allow the cuff 28 to slide over the bulbous urethra, and one suitable size for a width of the G is in the range of 0.4-2 cm. The gap G provides the rigid frame 30 with a C-shaped conformation in lateral cross-section such that the rigid frame 30 extends in an arc A from the first end 44 around to the second end 46. The extent of the arc A depends upon the selected width of the gap G, and suitable ranges for the size of the arc A are from about a half circle (~180 degrees) to slightly less than a full circle (less than 360 degrees). For example, suitable preferred ranges for the size of the arc A are from 270-330 degrees.

The inflatable balloon 32 is generally inflated to a pressure in a range from 40-120 cm H2O. One suitable pressure for cuff inflation is about 65 cm H2O. The rigid frame 30 is configured to resist deformation or expansion of the cuff 28 when the inflatable balloon 32 is inflated, which could undesirably displace the cuff 28 from the urethra. With this in mind, the rigid frame 30 is fabricated from a material that is configured to resist expanding in the presence of a pressure applied to the rigid frame 30 of less than about 150 cm H2O. In this manner, the rigid frame 30 does not expand in a noticeable way or to meaningful degree even as the inflatable balloon 32 is inflated to a pressure of about 120 cm H20. In engineering terms, the rigid frame has negligible stress in response to a strain arising from a pressure applied to the interior of the rigid frame 30 of up to 150 cm H2O. Suitable materials for fabricating the rigid frame 30 include stainless steel, titanium, ceramic, high impact polymers, nylon, polyetherimide, polyurethane, or polypropylene. When the rigid frame 30 is fabricated from a metal, the thickness of the metal is suitably selected to be about 0.2-2 mm. When the rigid frame is fabricated from a polymer, the thickness of the polymer as suitably selected to be about 0.5-3 mm.

The inflatable balloon 32 is placed to capture the urethra between inflatable balloon 32 and the interior surface 34 of the rigid frame 30 when the balloon 32 is inflated. The inflatable balloon 32 is fabricated from a flexible and elastic material such as silicone or polyurethane or the like. Since the inflatable balloon 32 is inflated with saline, it is preferable that the inflatable balloon is occlusive or resistant to leaking (or leak proof) over the range of useful inflation pressures.

Figure 3A:
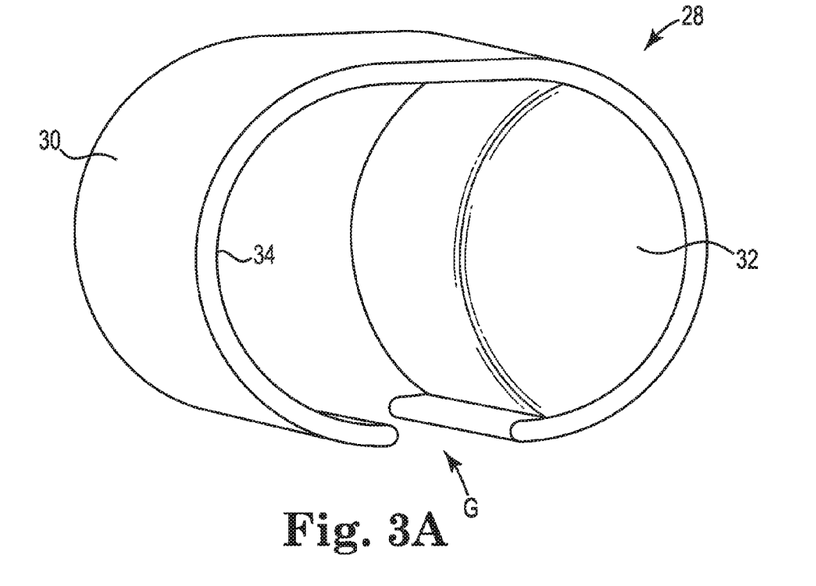
FIG. 3A is a perspective view of the cuff illustrated in FIG. 2 showing an inflated balloon attached to a lateral side of an interior frame of the cuff.
Figure 3B:
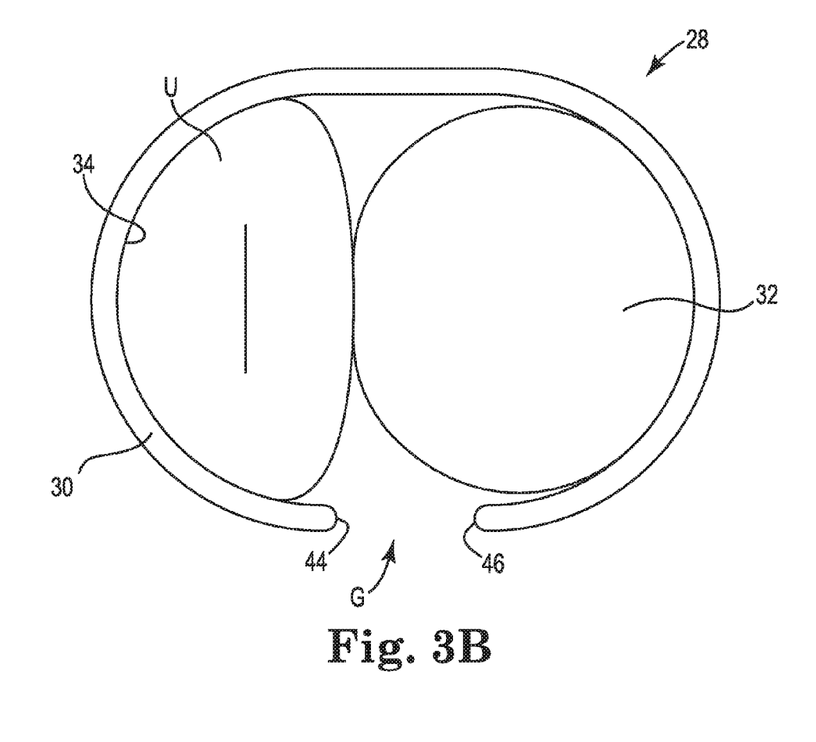
FIG. 3B is an end view of the cuff illustrated in FIG. 3A with the inflated balloon coapting a urethra.

FIG. 3A is a perspective view and FIG. 3B is an end view of one embodiment of the cuff 28. The gap G is spaced apart between the gap ends 44, 46, where the gap G is sized to be placed over an outside diameter of a bulbous urethra. The inflatable balloon 32 is illustrated in its inflated state that is sized to press and contain the urethra U (FIG. 3B) against the interior surface 34 of the frame 30. The cuff 28 is configured to coapt the urethra U when the inflatable balloon 32 is inflated to a pressure that the surgeon has pre-surgically determined to suitably coapt the urethra U.

FIG. 3B illustrates the inflatable balloon 32 is configured to inflate to occupy substantially all of a volume of one side (or lateral section) of the frame 30 to thus coapt the urethra U against the opposing interior surface 34 of the frame 30. For example, if the cuff 28 is viewed to have bilateral symmetry to the left and the right of the gap G as illustrated in FIG. 3B, the inflated balloon 32 occupies the right hand lateral section in pressing and coapting the urethra U into the left hand lateral section of the cuff 28.

In one embodiment, the cuff 28 is placed around a portion of the urethra with the gap G located anterior to the urethra U, for example after the surgeon dissects tissue around the urethra U in a typical implantation approach.

In one embodiment, the cuff 28 is placed around a portion of the urethra with the gap G located posterior to the urethra U through an implantation approach that includes dissecting tissue anteriorly around about 270 degrees of the urethra. In this approach, some tissue remains attached to the posterior urethra. The tissue attached to the posterior urethra stabilizes the urethra and reduces the risk of the surgeon unintentionally dissecting into the urethral tissue.

FIGS. 4A-6B illustrate advantageous embodiments of cuffs that may be surgically implanted around an anterior portion of the urethra, which allows the surgeon to selectively dissect only the visible tissue that is located anterior and laterally to the sides of the urethra while leaving the urethra attached to the supporting tissue behind or posterior to the urethra.

Figure 4A:
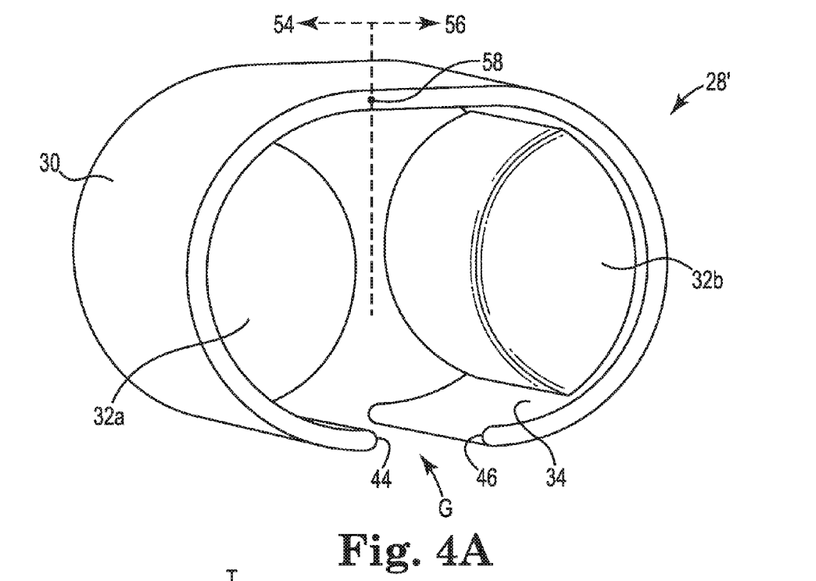
FIG. 4A is a perspective view of one embodiment of a cuff suitable for use with the system illustrated in FIG. 1, where the cuff includes two inflatable balloons shown in an inflated state.
Figure 4B:
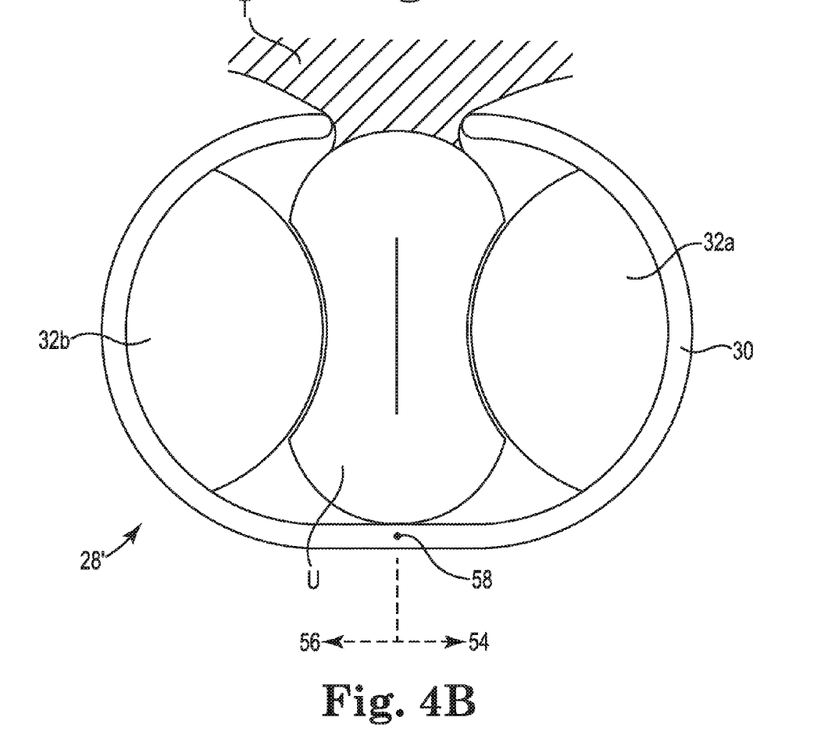
FIG. 4B is an end view of the cuff illustrated in FIG. 4A with the inflated balloons coapting a urethra.

FIG. 4A is a perspective view and FIG. 4B is an end view of one embodiment of a cuff 28' provided with a pair of opposing inflatable balloons 32a, 32b. Each of the balloons 32a, 32b is attached to the interior surface 34 of the rigid frame 30. For example, in the embodiment of FIG. 4, the first inflatable balloon 32a is attached to the interior surface 34 of a first lateral section 54 (FIG. 4B) of the cuff 28' and the second inflatable balloon 32b is attached to the interior surface 34 of a second lateral section 56 of the cuff 28'. In the specific embodiment of FIG. 4, the first inflatable balloon 32a is attached to the interior surface 34 of the first lateral section 54 of the frame 30 between the slot formed by the gap G and a midpoint 58 of the frame 30 that is opposite of the slot/gap G, and likewise the second inflatable balloon 32b is attached to the interior surface 34 of the second lateral section 56 of the frame 30 between the slot/gap G and the midpoint 58 of the frame 30. The balloons 32a, 32b are positioned to provide opposing pressure to the urethra U upon inflation. Each of the balloons 32a, 32b includes a conduit connector (not shown) that is attachable to the tubing 24 (FIG. 1) to allow the balloons 32a, 32b to be inflated with saline or other liquid.

With reference to FIG. 4B, the cuff 28' is placed around an outside anterior portion of the urethra, preferably with the balloons 32a, 32b in their deflated state. This allows the surgeon to fully visualize placement of the cuff 28' over the anterior portion of the urethra. In addition, the surgeon need not dissect the complete circumference around the urethra prior to placing the cuff 28'. One exemplary gap G is illustrated having a gap size of about 30 degrees, such that the frame 30 extends in an arc of about 330 degrees over the 330 degrees of tissue dissection around the urethra. Some gap G sizes are about 90 degrees, allowing the surgeon to not dissect that portion of tissue T posterior to the urethra that is difficult to see. After implantation and after the balloons 32a, 32b are inflated they provide uniform lateral pressure to the urethra U, which uniformly coapts the urethra U to provide the user with a continent state.

Figure 5A:
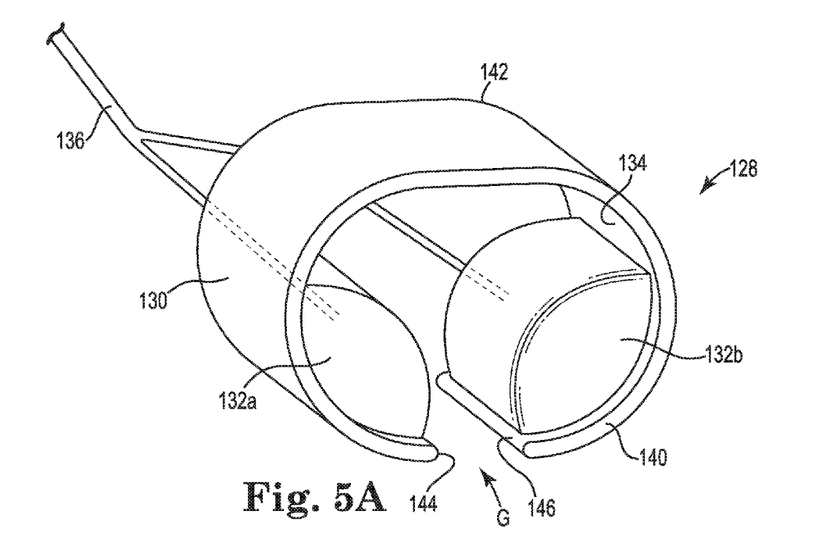
FIG. 5A is a perspective view of one embodiment of a cuff suitable for use with the system illustrated in FIG. 1, where the cuff includes two balloons attached in separate quadrants of the cuff.
Figure 5B:
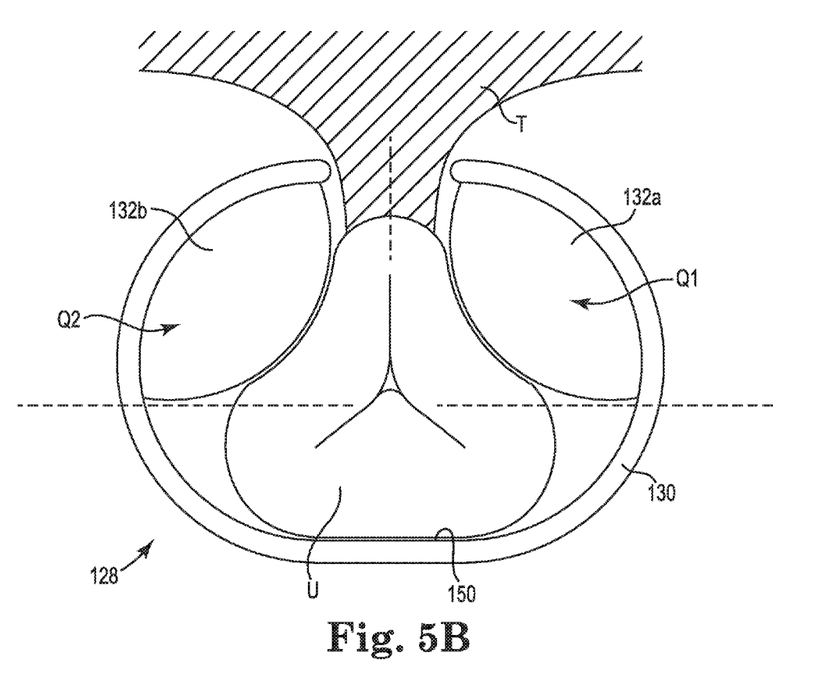
FIG. 5B is an end view of the cuff illustrated in FIG. 5A with inflated balloons coapting a urethra.

FIG. 5A is a perspective view and FIG. 5B is an end view of one embodiment of a cuff 128 having two inflatable balloons attached in separate quadrants Q1, Q2 of the cuff 128.

The cuff 128 includes a rigid frame 130 with two inflatable balloons 132a, 132b attached to an interior surface 134 of the rigid frame 130. The inflatable balloons 132a, 132b are provided with a Y-shaped connector 136 that is suitable for attachment to the tubing 24 (FIG. 1). Other suitable connectors attachable to the tubing 24 (FIG. 1) are also acceptable.

The cuff 128 includes a gap G that is formed from a top edge 140 to a bottom edge 142 of the rigid frame 130, such that the gap G extends between a first end 144 and a second end 146 of the frame 130. The G is sized to allow the cuff 28 to slide over the anterior portion of the urethra that has been exposed by dissection of the tissue T. The stiffness or robustness of the rigid frame 130 allows the cuff 28 to stablize the urethra and contain the pressurization of the balloons 132a, 132b. The gap G and the arc of the frame 130 are similar to the gap and the arc A of the frame 30 described above.

The first inflatable balloon 132a is attached to the interior surface 134 from the first end 144 of the gap G over the first quadrant Q1 of the rigid frame 130, and the second inflatable balloon 132b is attached to the interior surface 134 from the second end 146 of the gap G over the second quadrant Q2 of the rigid frame 130.

FIG. 5B illustrates one advantage of the cuff '28 in that inflation of the balloons 132a, 132b squeezes the urethra U into the frame 130 and away from the gap G, which ensures that the urethra U is contained within the frame 130 as the cuff 128 is cycled between the deflated (urine allowed to pass) state and the inflated (urethra coapted) state. Inflation of the balloons 132a, 132b presses the urethra U against a back portion 150 of the frame 130 to increase the coaptation of the urethra U and to ensure that the urethra U is contained within the frame 130 during cycling of the cuff 128.

Figure 6A:
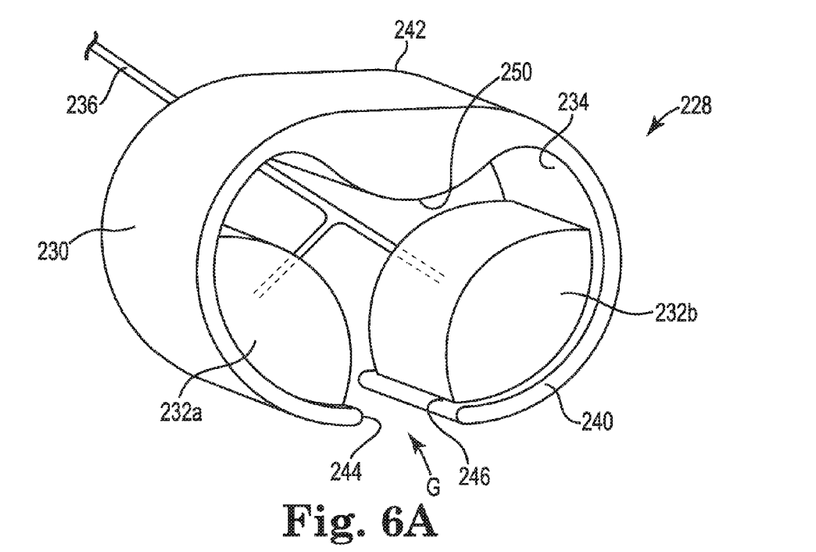
FIG. 6A is a perspective view of one embodiment of a cuff suitable for use with the system illustrated in FIG. 1, where the cuff includes two inflatable balloons and a convex lobe.
Figure 6B:
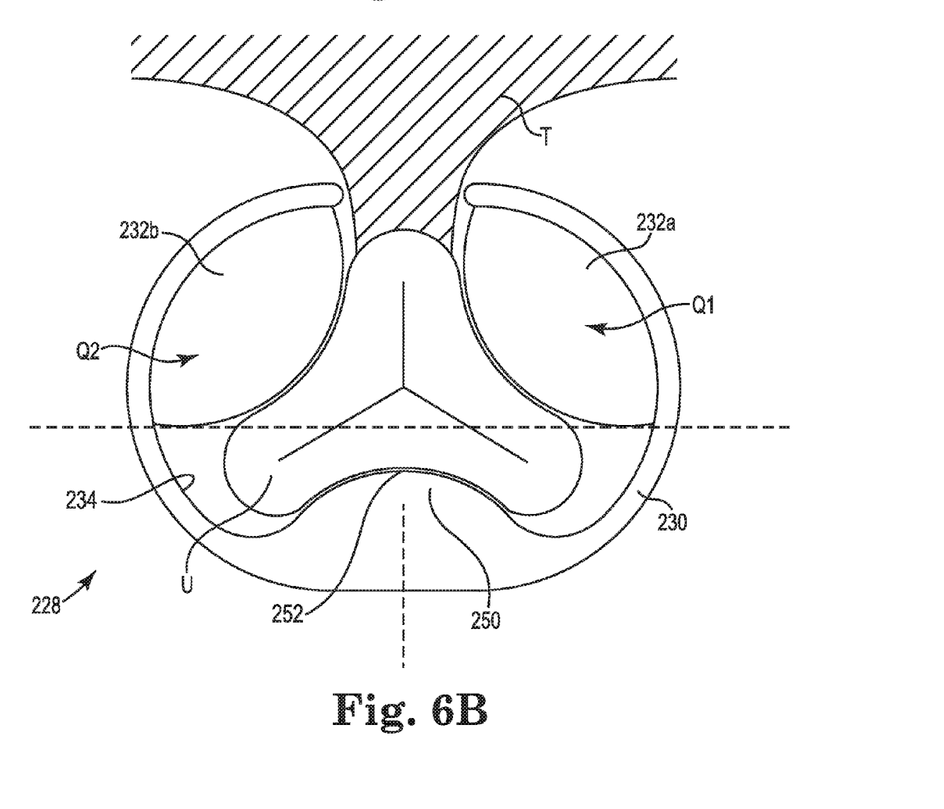
FIG. 6B is an end view of the cuff illustrated in FIG. 6A with inflated balloons cooperating with the convex lobe to coapt a urethra.

FIG. 6A is a perspective view and FIG. 6B is an end view of another embodiment of a cuff 228 having two inflatable balloons 232a, 232b attached in separate quadrants Q1, Q2 to an inside surface 234 of a rigid frame 230 of the cuff 228. The inflatable balloons 23a, 232b are provided with a Y-shaped connector 236 that is suitable for attachment to the tubing 24 (FIG. 1).

The cuff 228 includes a gap G that is formed from a top edge 240 to a bottom edge 242 of the rigid frame 230, such that the gap G extends between a first end 244 and a second end 246 of the frame 230 to provide the cuff 228 with a C-shape in lateral cross-section. The G is sized to allow the cuff 228 to slide over the anterior portion of the urethra that has been exposed during tissue dissection, as described above. In this regard, the gap G and the arc of the frame 230 are similar to the gap and the arc A of the frame 30 described above.

With reference to FIG. 6B, the interior surface 234 of the frame 230 includes a convex lobe 250 located at a midpoint 252 of the frame 230 opposite of the slot formed by the gap G. The convex lobe 250 extends longitudinally from the top edge 240 to the bottom edge 242 of the rigid frame 230 and projects into or inside of the frame 230. The first inflatable balloon 132a is attached to the interior surface 134 from the first end 144 of the gap G over the first quadrant Q1 of the rigid frame 130, and the second inflatable balloon 132b is attached to the interior surface 134 from the second end 146 of the gap G over the second quadrant Q2 of the rigid frame 130. This locates the balloons 232a, 232b a uniform distance away from the lobe 250. For example, where the top edge 240 and the bottom edge 242 of the band or the frame 230 each extends along an arc of more than 270 degrees and less than 330 degrees, the first inflatable balloon 232a will be spaced apart from the convex lobe 250 by 135 degrees on a first side of the frame 230 (e.g., in quadrant Q1) and the second inflatable balloon 232b will be spaced apart from the convex lobe 250 by 135 degrees on a second side of the frame 230 (e.g., in quadrant Q2).

FIG. 6B illustrates one advantage of the cuff 228 in that inflation of the balloons 232a, 232b squeezes the urethra U into the lobe 250 at the back portion of the frame 230, which ensures that the urethra U is contained within the frame 230 as the cuff 128 is cycled between the deflated (urine allowed to pass) state and the inflated (urethra coapted) state. In addition, the lobe 250 contributes geometrically to the coaptation of the urethra U as the balloons 232a, 232b press the urethra U into the lobe 250. This will increase the coaptation of the urethra U and offers full closure of the urethra U at balloon pressures lower than the usual pressure of about 65 cm H2O.

Figure 7A:
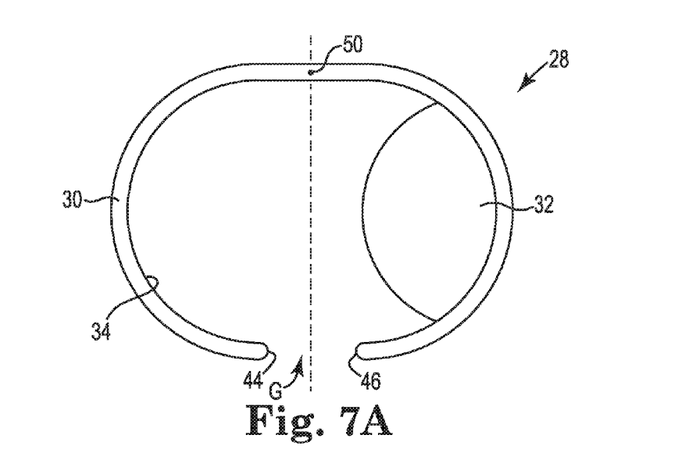
FIG. 7A is an end view of the cuff illustrated in FIG. 3A showing one inflatable balloon attached to a first lateral section in a frame of the cuff.
Figure 7B:
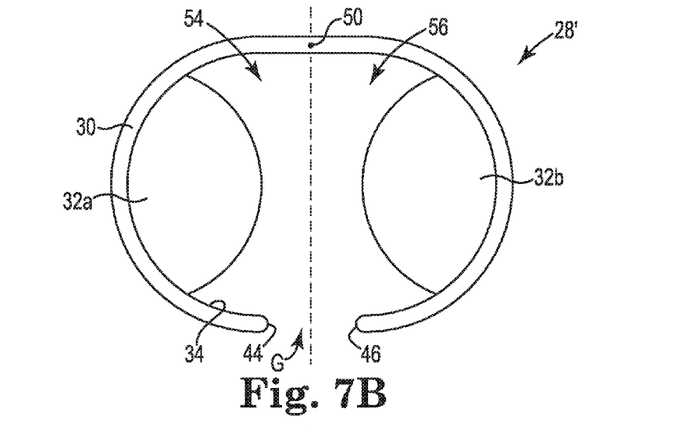
FIG. 7B is an end view of the cuff illustrated in FIG. 4A showing two inflatable balloons, each attached to a different lateral section in a frame of the cuff.
Figure 7C:
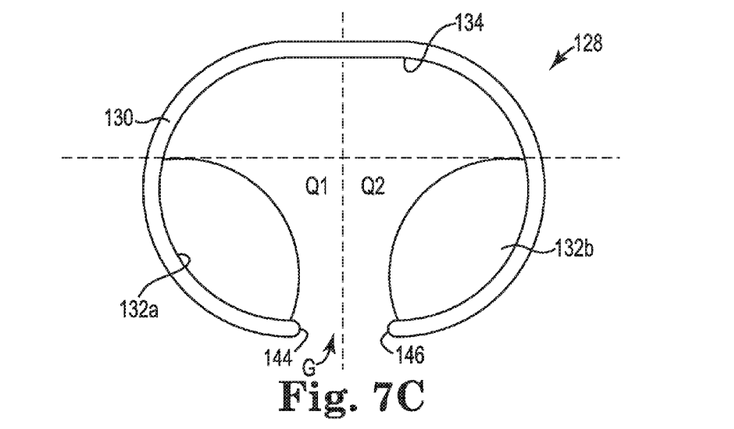
FIG. 7C is an end view of the cuff illustrated in FIG. 5A showing two inflatable balloons, each attached to a different quadrant inside a frame of the cuff.

FIG. 7A-FIG. 7C illustrate various embodiments of an inflatable cuff for an AUS system.

FIG. 7A illustrates the cuff 28 provided with one inflatable balloon 32 that is located between one end 46 of the gap G and a midpoint 50 of the frame 30. The inflatable balloon 30 is suitably attached to the frame 30 anywhere in the first lateral section between the end 46 and the midpoint 50.

FIG. 7B illustrates the cuff 28' provided with two inflatable balloons 32a, 32b. Each inflatable balloon is located in one lateral half of the frame 30. For example, the first balloon 32a is located in the left lateral half and is attached to the frame 30 between one end 44 of the gap G and the midpoint 50, and the second balloon 32b is located in the right lateral half and is attached between the other end 46 and the midpoint 50. FIG. 7B illustrates that the inflatable balloons 32a, 32b laterally oppose one another. However, the inflatable balloons 32a, 32b are each suitably located anywhere in its own respective lateral half of the frame 30.

FIG. 7C illustrates the cuff 128 provided with the first inflatable balloon 132a attached to the frame 130 in the first quadrant Q1 and the second inflatable balloon 132b attached to the frame 130 in the second quadrant Q2. In geometric terms, each balloon is attached to the frame between one of the respective ends 144, 146 and a location that is displaced from the end by about 90 degrees (or π/4 radians).

The AUS system 20 is implanted into the patient at the location illustrated in FIG. 1, for example through the following surgical procedure.

Figure 8A:
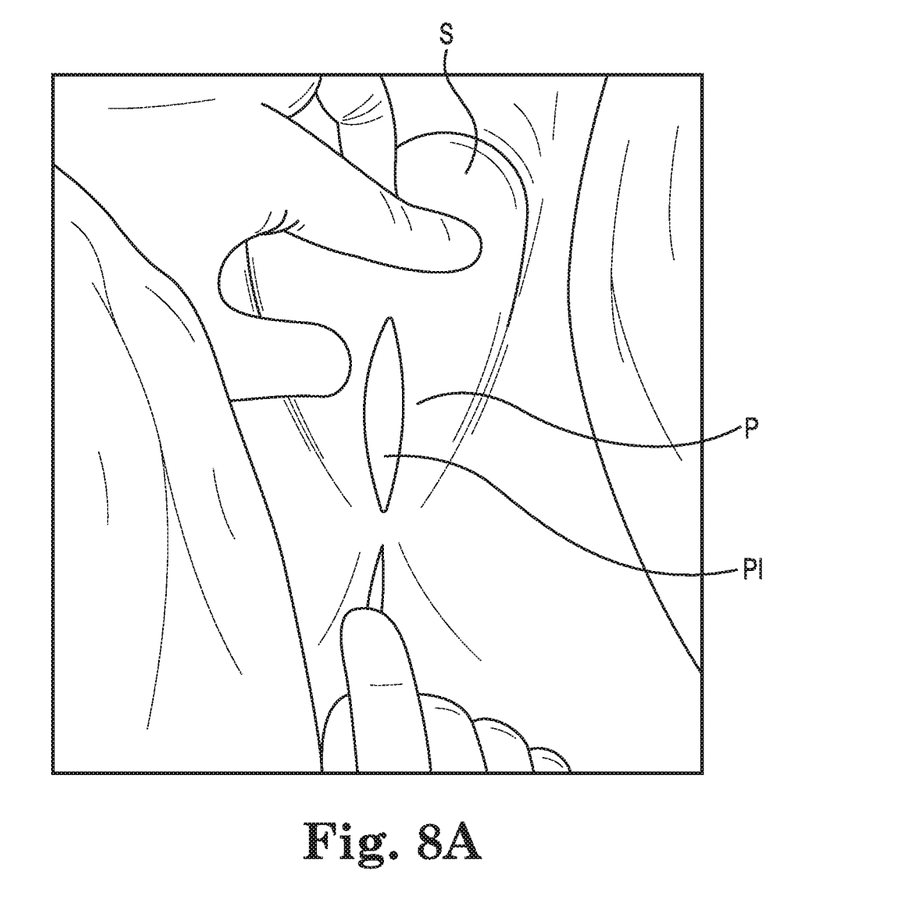
FIG. 8A is a schematic view and FIG. 8B is a front view of tissue dissection in preparation for placement of an embodiment of a cuff of the AUS system.

FIG. 8A illustrates the surgeon using his or her index finger and thumb to elevate the scrotum S as a perineal incision PI is formed in the perineum P.

Figure 8B:
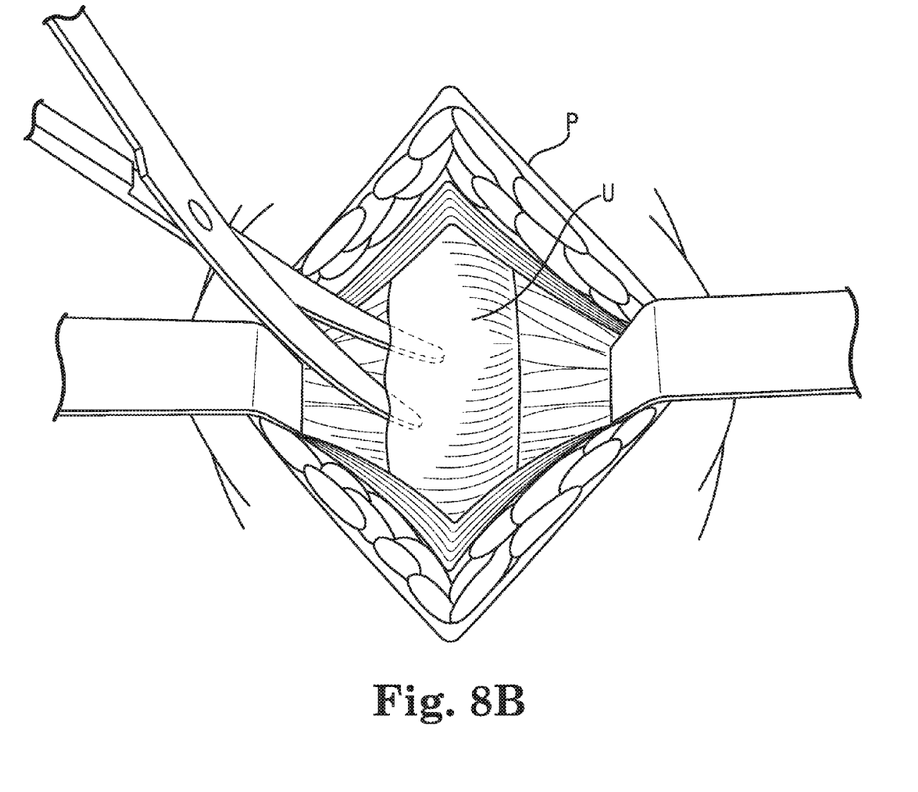

FIG. 8B is a schematic view of the tissue in the region of the perineum P dissected and retracted to expose the urethra U. The tissue is dissected away from the anterior side of the urethra U through the use of a suitable instrument, dissecting tissue on each lateral side but leaving the tissue posterior to the urethra intact. There is an advantage to dissecting only that tissue that is visible to the surgeon; one is that it saves time, and two is that dissection of the posterior tissue includes some risk in that the surgeon has an imperfect view of the tissue behind urethra. Advantageously, during implantation the surgeon dissects the tissue anterior to and lateral to the urethra in a range of about 180 to 330 degrees, which is the range of visible tissue around the urethra, and which leaves a section of tissue posterior to the urethra intact and attached to the posterior urethra.

Figure 8C:
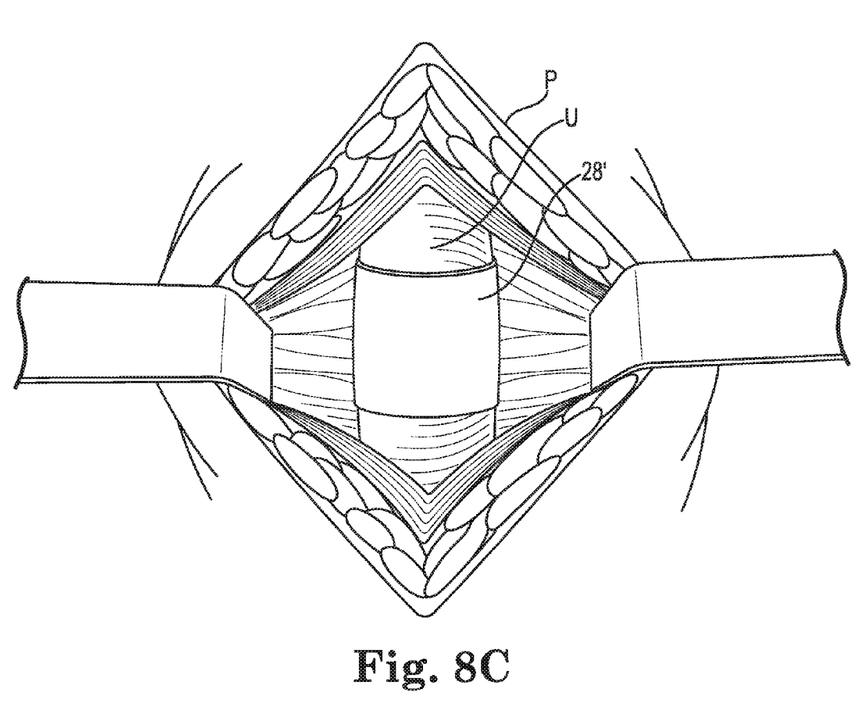
FIG. 8C is a front view of an embodiment of a cuff of the AUS system placed around an outer diameter of a urethra.

FIG. 8C is a schematic view of the cuff 28' placed around the urethra U. The gap G has been employed to pass the cuff 28' over the outside diameter of the urethra U, after which the gap G of the cuff 28' is located behind or posterior to the urethra U. In this manner, the gap G allows the surgeon to selectively dissect only that tissue that is visible when viewing the anterior side of the urethra.

Figure 8D:
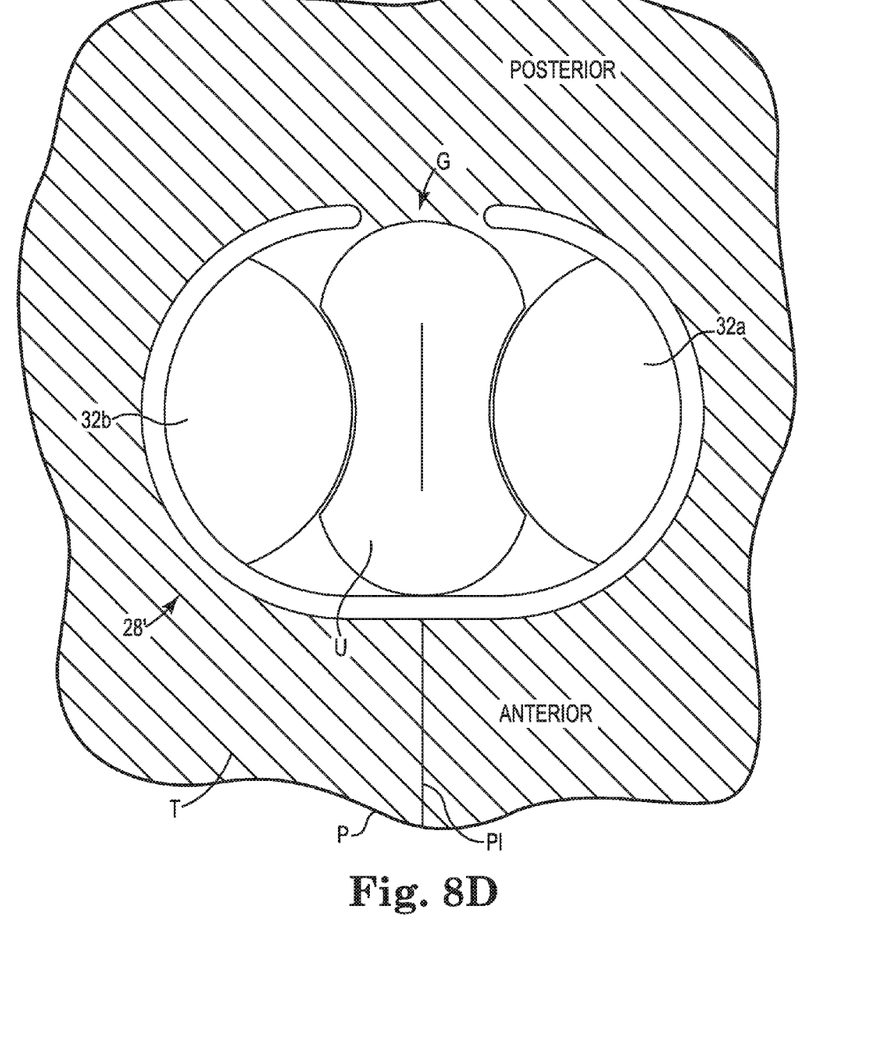
FIG. 8D is a schematic cross-sectional view of the cuff illustrated in FIG. 8C surrounded by tissue.

FIG. 8D illustrates a schematic cross-sectional view of the cuff 28' after implantation and closure of the perineal incision PI. The cuff 28' is effectively surrounded by tissue T which contributes to retaining the cuff 28' around the urethra U during the life cycle of the system 20.

Embodiments of various cuffs of an AUS system have been described in this application that provide easier placement of the cuff around the anterior portion of the urethra in a manner that obviates dissecting the tissue posterior the urethra that is blocked from the surgeon's view. The balloons of the cuff expand into an interior space of the frame and are configured to have reduced or eliminated kinking.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A cuff of an artificial urinary sphincter system, the cuff comprising:
   a frame having a first end spaced away from a second end by a gap, where the gap extends from a top edge to a bottom edge of the frame to provide an opening in the frame sized to allow the frame to be placed around a portion of a urethra, where the frame has a frame length measured along an interior surface of the frame from the first end to the second end of the frame to define a first quadrant that extends from the first end for a distance of about 25% of the frame length and a second quadrant that extends from the second end for a distance of about 25% of the frame length;
   a first inflatable balloon attached to the interior surface of the frame in the first quadrant of the frame; and
   a second inflatable balloon attached to the interior surface of the frame in the second quadrant of the frame;
   wherein the first inflatable balloon is separate from and spaced apart from the second inflatable balloon;
   wherein an entirety of the first inflatable balloon is located in the first quadrant of the frame.

2. The cuff of claim 1, wherein the gap provides the frame with a C-shaped conformation in lateral cross-section.

3. The cuff of claim 1, wherein the gap provides the frame with a C-shaped conformation in lateral cross-section, and the C-shaped conformation in lateral cross-section extends along an arc of more than 270 degrees and less than 360 degrees.

4. The cuff of claim 1, wherein the interior surface of the frame includes a convex lobe extending from the top edge to the bottom edge of the frame with the convex lobe located opposite of the gap.

5. The cuff of claim 1, wherein the frame is a rigid frame that is resistant to flexing such that a width of the gap between the first end and the second end of the frame remains substantially unchanged for a pressure applied to the interior surface of the rigid frame of less than 120 cm H2O.

6. The cuff of claim 1, wherein the top edge and the bottom edge of the frame each extend along an arc of more than 180 degrees and less than 330 degrees.

7. The cuff of claim 1, wherein the top edge and the bottom edge of the frame each extend along an arc of more than 270 degrees and less than 330 degrees.

8. A cuff of an artificial urinary sphincter system, the cuff comprising:
   a C-shaped frame provided with a slot that bisects the frame into a first lateral section and a second lateral section, the slot sized to have a width that allows the slot to pass over an outside diameter of a urethra to allow the frame to be placed around a portion of the urethra; and
   an inflatable balloon attached to an interior surface in the first lateral section of the frame between the slot and a midpoint of the frame opposite of the slot;
   wherein the inflatable balloon is configured to inflate to occupy substantially all of a volume of the first lateral section of the frame to thus coapt the urethra within the second lateral section of the frame against an interior surface of the second lateral section of the frame.

9. The cuff of claim 1, wherein an entirety of the second inflatable balloon is located in the second quadrant of the frame.

* * * * *